United States Patent [19]

Detz

[11] 4,161,495

[45] Jul. 17, 1979

[54] METHOD FOR STABILIZING ACETYLENE

[75] Inventor: Clifford M. Detz, White Plains, N.Y.

[73] Assignee: Union Carbide Corporation, New York, N.Y.

[21] Appl. No.: 945,550

[22] Filed: Sep. 25, 1978

[51] Int. Cl.$^2$ .................... C07C 11/24; C07C 7/18
[52] U.S. Cl. .................... 585/4; 48/197 FM; 203/9; 203/50; 203/67; 208/48 AA; 585/2; 585/6
[58] Field of Search ............ 260/666.5, 679 R, 679 A; 48/197 FM; 203/9, 50, 67

[56] References Cited

U.S. PATENT DOCUMENTS

| | | | |
|---|---|---|---|
| 3,226,213 | 12/1965 | Nelson et al. | 48/197 FM |
| 3,527,822 | 9/1970 | Benson | 260/666.5 |
| 3,557,232 | 1/1971 | Starnes | 260/666.5 |
| 3,861,160 | 1/1975 | Walker | 48/197 FM |
| 3,964,979 | 6/1976 | Watson | 203/9 |

*Primary Examiner*—Delbert E. Gantz
*Assistant Examiner*—George E. Schmitkons
*Attorney, Agent, or Firm*—John R. Doherty

[57] ABSTRACT

A method for stabilizing acetylene against explosive decomposition comprising mixing together with the acetylene a chemical free radical scavenging agent chosen from the group consisting of nitric oxide, hydrogen chloride, hydrogen bromine, hydrogen iodide and vinyl bromine as well as mixtures thereof.

7 Claims, 1 Drawing Figure

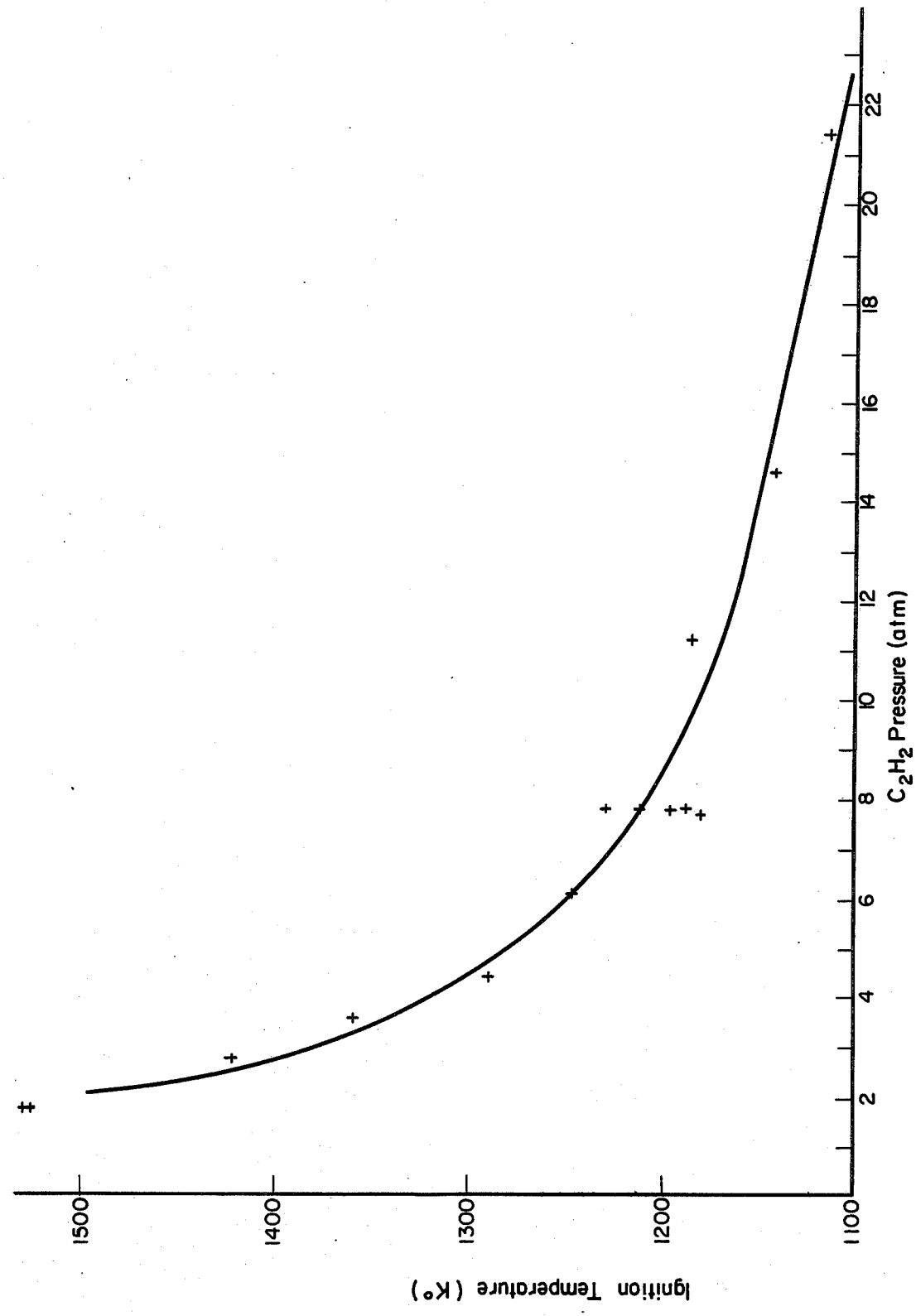

METHOD FOR STABILIZING ACETYLENE

METHOD FOR STABILIZING ACETYLENE

The present invention relates to a method for stabilizing acetylene against explosive decomposition.

BACKGROUND OF THE INVENTION

Acetylene is a commercially important gas which is widely used and extensively distributed. Because acetylene is thermodynamically unstable with respect to its decomposition into carbon and hydrogen, it will decompose explosively when subject to a suitable ignition source. An explosive decomposition can occur even in the absence of an oxidizing agent such as air or oxygen. For this reason, elaborate precautions must be taken to insure that acetylene is not exposed to ignition sources during shipment or storage.

Acetylene is commonly shipped in special containers in which the acetylene is dissolved in a solvent, such as acetone or dimethylformamide, and this solution is dispersed in a porous, inert filler heat sink material, such as calcium silicate. These containers are commonly fitted with flash arrestors and fusible plugs to limit the danger of explosion. Despite these precautions, the pressure of acetylene gas which can be tolerated over the acetylene solutions in these containers is limited to about 15 atm at 23° C. At pressures higher than about 15 atm, the combined thermal mass of the solution, the solvent and the inert filler heat sink material is not great enough to prevent an explosive decomposition from propagating through the container once it has been initiated.

A similar situation exists in pipelines which are used to transport acetylene gas. Acetylene is transported as a gas in such pipelines at pressures which must be limited to less than about 1.5 atm. To minimize the danger of explosion or to limit the extent of an explosion, these pipelines are often filled with inert material, such as raschig rings, and they are fitted with flash arresting devices to limit the propagation of explosions.

Common sources for the ignition of acetylene are: sparks, flashbacks from torches or flames, and hot walls of containers or pipes produced by the inadvertent application of external heat sources. In general, explosive decompositions are initiated in the gas phase. In acetylene containers, this decomposition can then propagate through the solution and filler resulting in rupture of the container. It is desirable, therefore, to insure that the gas phase acetylene be rendered as stable as possible. This can be accomplished, for example, by reducing the pressure of the acetylene gas. p It is known that the partial pressure of acetylene gas at a given total pressure can be effectively reduced while at the same time providing an additional heat sink if an inert gas, such as nitrogen or carbon dioxide, is mixed with the acetylene. Thus if a mixture at a total pressure of 10 atm consists of a partial pressure of acetylene of 9 atm and a partial pressure of $N_2$ of 1 atm, the ignition behavior of such a mixture is nearly identical to that of pure acetylene at a pressure of 9 atm.

SUMMARY OF THE INVENTION

It has been found in accordance with the present invention that certain gas-phase additives have an effect upon the ignition of acetylene which is profoundly greater than that of an equivalent amount of inert diluent. These additives exert a chemical effect which inhibits the ignition of acetylene, and such additives generally belong to a class of materials which are known to scavenge free radicals in gas phase chemical reactions. It is postulated that the effect of these inhibitors is due to their ability to unite with free radicals which are thought to be present during the initiation and propagation stages of the acetylene decomposition. The inhibitors which have proven to be effective in the practice of the invention are the compounds, NO, HCl, HBr, HI, and $C_2H_3Br$. The amount of these materials which is required is between 0.5% and 10% mole fraction when mixed with acetylene gas.

Accordingly, it is an object of the present invention to provide an improved method for stabilizing acetylene against explosive decomposition.

Another object of the present invention is to provide an improved method for stabilizing acetylene which is effective in inhibiting the ignition of acetylene and which improves safety in handling, shipping and storage of the acetylene.

Still another object of the present inventors is to provide an improved method for stabilizing acetylene against explosive decomposition by mixing the acetylene with relatively small quantities of chemically stabilizing agents.

BRIEF DESCRIPTION OF THE DRAWING

The sole FIGURE in the accompanying drawing is a curve showing the relationship between the ignition temperature of pure acetylene and partial pressure at a specified temperature, i.e. 23° C.

DESCRIPTION OF PREFERRED EMBODIMENTS

The ignition temperatures for pure acetylene and mixtures of acetylene with additives can readily be determined by immersing an inert metal wire, e.g. platinum, in the gas or gas mixture and heating the wire until ignition occurs. The temperature of the wire can be continuously monitored as the wire is being heated and in this manner a direct determination of the ignition temperatures can be attained.

In FIG. 1, the curve shows the measured ignition temperature of pure acetylene as a function of its partial pressure at 23° C. (see "Threshold Conditions for the Ignition of Acetylene Gas by a Heated Wire," by C. M. Detz, *Combustion and Flame*, Vol. 26, page 25-1976). The solid curve is a least squares fit of the experimental data to the form:

$$\ln C = 209.3 + 4.22 \times 10^{-4}/T_i + 24.43 \, T_i \quad (1)$$

$$C = \left[ \frac{24.45}{P} - .151 \right]^{-1} \text{mole/liter}$$

where:
P is pressure of acetylene in atm.
$T_i$ is ignition temperature in °K., and
C is acetylene gas concentration in mole/liter The ignition temperatures for mixtures of acetylene and additives can be determined and compared to the ignition temperatures given by Equation (1) above for the equivalent partial pressures of acetylene, and a factor $\Delta T_i$ can be calculated. $\Delta T_i$ is the difference between the ignition temperature determined for the mixture and that determined for pure acetylene at a pressure equal to the partial pressure of acetylene in the mixture. Additives which stabilize acetylene will have positive values of $\Delta T_i$. Additives which are inert will have $\Delta T_i$ values of zero within experimental error, while additives which destabilize acetylene will have negative values of $\Delta T_i$.

Example I

Sample mixtures of acetylene and carbon dioxide were prepared and tested. The amount of $CO_2$ in the mixtures was varied from about 0.6 to 4.7% mole fraction and the mixtures were maintained at partial pressures ranging from about 5.2 to 7.5 atm. The ignition temperature for each sample mixture was determined in accordance with the procedure outlined above and the $\Delta T_i$ value for each mixture was then calculated. Table 1 below shows the results of this test.

Table 1:

| Effect of $CO_2$ on Acetylene Ignition | | | |
|---|---|---|---|
| $C_2H_2$ Pressure (ATM) | %$CO_2$ | Ignition Temp. (K) | $\Delta T_i$ (K) |
| 5.23 | 4.7 | 1279 | −8 |
| 6.65 | .84 | 1250 | +12 |
| 6.76 | .64 | 1222 | +9 |
| 7.45 | 4.5 | 1224 | +9 |

It will be noted that the $\Delta T_i$ values for the mixtures do not significantly differ from zero. Thus, this example establishes that inert additives such as $CO_2$ do not significantly affect the ignition temperature of acetylene at a given acetylene partial pressure.

In the following examples, mixtures of acetylene with chemically inhibiting additives, e.g. nitric oxide, hydrogen halides and vinyl bromide, were also prepared and tested. The results of these tests should be compared to the ignition behavior of the acetylene-carbon dioxide mixture given above.

Example II

Sample mixtures of acetylene and nitric oxide were made wherein the percent mole fraction of NO in the mixtures was varied from about 0.7 to 10.7%. In the tests, the mixtures were maintained at partial pressures ranging from about 1.6 to about 22.2 atm. Again the ignition temperature for each mixture was determined in accordance with the procedure outlined above. Table II below shows the data from these tests.

Table 2:

| Effect of NO on Acetylene Ignition | | | |
|---|---|---|---|
| $C_2H_2$ Pressure (ATM) | %NO | Ignition Temp. (K) | $\Delta T_i$ |
| 4.41 | .72 | 1320 | +22 |
| 7.88 | .86 | 1234 | +14 |
| 14.49 | .80 | 1173 | +51 |
| 21.24 | .80 | 1169 | +57 |
| 1.65 | 5.2 | 1563 | −5 |
| 1.66 | 4.2 | 1551 | −17 |
| 1.68 | 4.3 | 1542 | −26 |
| 4.36 | 5.3 | 1381 | +81 |
| 4.42 | 4.8 | 1376 | +77 |
| 4.56 | 4.1 | 1364 | +71 |
| 7.65 | 4.8 | 1309 | +95 |
| 7.86 | 4.8 | 1344 | +114 |
| 10.93 | 4.8 | 1258 | +85 |
| 17.95 | 4.8 | 1244 | +114 |
| 19.09 | 4.9 | 1242 | +117 |
| 22.23 | 4.9 | 1233 | +115 |
| 4.54 | 9.1 | 1356 | +63 |
| 7.77 | 10.7 | 1271 | +49 |

It will be seen from this data that NO inhibits the explosive decomposition of acetylene for acetylene partial pressures in excess of about 2 atm. Nitric oxide concentrations of approximately 1%, 5%, and 10% are effective but the higher NO concentration give rise to a greater increase in the ignition temperature. The increase in ignition temperature caused by the added NO is a function of the acetylene pressure and levels off at acetylene pressures greater than about eight atmospheres. The maximum increase in ignition temperatures is 57° K. for 0.7% NO added and is 115° K. for 5% NO added. As indicated by the data for mixtures containing 9.1% and 10.7% NO, increasing the NO concentration above 5% does not produce an additional increase in the degree of inhibition which results from nitric oxide. In fact, mixtures containing 10% NO are apparently somewhat less stabilized than mixtures containing approximately 5%.

Example III

Sample mixtures of acetylene and several hydrogen halides, namely HCl, HBr and HI, were also prepared and tested. The amount of the hydrogen halide used in each mixture was varied from about 1.0 to 5.1% and the mixtures were maintained at partial pressures ranging from about 2.3 to about 15.0 atm. The ignition temperature for each of the mixtures was again determined in accordance with the procedure outlined above. The $\Delta T_i$ values were then calculated. Tables 3, 4, and 5 show the results of these tests for each of the acetylene mixtures containing HCl, HBr, HI, respectively.

Table 3:

| Effect of HCl on Acetylene Ignition | | | |
|---|---|---|---|
| $C_2H_2$ Pressure (ATM) | %HCl | Ignition Temp. (K) | $\Delta T_i$ |
| 5.37 | 1.0 | 1318 | +53 |
| 7.87 | 1.0 | 1226 | +16 |
| 14.99 | 1.0 | 1154 | +9 |
| 2.72 | 5.1 | 1448 | +53 |
| 4.32 | 5.0 | 1410 | +110 |
| 7.82 | 5.0 | 1338 | +128 |
| 14.90 | 5.0 | 1233 | +87 |

Table 4:

| Effect of HBr on Acetylene Ignition | | | |
|---|---|---|---|
| $C_2H_2$ Pressure (ATM) | %HBr | Ignition Temp. (K) | $\Delta T_i$ |
| 2.37 | 1.0 | 1512 | +82 |
| 4.38 | 1.0 | 1420 | +122 |
| 7.81 | 1.0 | 1323 | +112 |
| 14.86 | 1.0 | 1251 | +105 |
| 2.35 | 4.9 | 1588 | +155 |
| 4.41 | 4.9 | 1471 | +174 |
| 7.83 | 4.9 | 1370 | +160 |
| 14.7 | 5.1 | 1306 | +158 |

Table 5:

| Effect of HI on Acetylene Ignition | | | |
|---|---|---|---|
| $C_2H_2$ Pressure (ATM) | %HI | Ignition Temp. (K) | $\Delta T_i$ |
| 4.41 | 1.0 | 1286 | −12 |
| 7.89 | 1.0 | 1217 | +7 |
| 14.93 | 1.0 | 1188 | +40 |
| 2.7 | 4.8 | 1481 | +86 |
| 4.27 | 5.0 | 1387 | +82 |
| 7.74 | 5.0 | 1276 | +63 |
| 14.95 | 5.0 | 1196 | +50 |

It will be observed from this data that the hydrogen halides employed in the acetylene mixture in amounts ranging from about 1-5% were effective inhibitors of acetylene ignition. Generally speaking, hydrogen bromide is more effective than either hydrogen chloride or hydrogen iodide while hydrogen chloride is more effective than hydrogen iodide. Hydrogen iodide is, of course, the least effective.

It will be furthermore noted that when 5% HCl was added to acetylene, the mixture was stabilized over the pressure range 2–15 atm and the average increase in ignition temperature was 95° K. In the case of mixtures with 1% added HCl, significant stabilization occurred at pressure below about 5 atm.

Hydrogen bromide stabilized acetylene mixtures containing acetylene at 2–15 atm pressure at both 1% and 5% HBr. The average increase in ignition temperature was 105° K. for mixtures containing about 1% HBr and 162° K. for mixtures containing 5% HBr.

Hydrogen iodide is an effective stabilizing agent when present at levels of about 5% in mixtures containing acetylene at 2–15 atm. The average increase in the ignition temperature is about 70° K.

It should be understood that interpretation of the above stabilization data is complicated by the fact that the hydrogen halides can both react with acetylene and also decompose on the heated filiment. In a further test, a mixture of acetylene at 6.8 atm with 4.7% HBr added was prepared and analyzed by infrared spectroscopy. The mixture contained approximately 1% $C_2H_3Br$ indicating that approximately 20% of the HBr could react with the acetylene. It was also shown that HBr could decompose on the heated ignition wire to a significant extent. A platinum filiment was heated to 1100° C. for nine minutes in the presence of HBr at 1.6 atm. The pressure after exposure to the heated filiment dropped to 1.2 atm and there was a visible deposit of bromine in the vessel. Analysis of the gas which had been exposed to the heated filiment indicated that it contained 24.6% $H_2$. These results indicated that 57% of the HBr had decomposed.

Example IV

Sample mixtures of acetylene and vinyl bromide were also prepared and tested. The vinyl bromide was added to the mixtures in amounts of about 5.0% and the mixtures were maintained at partial pressures ranging from about 4.3 to about 14.8 atm. Table 6 shows the results of the ignition test using this acetylene-vinyl bromide mixture.

Table 6:

| | Effect of $C_2H_3Br$ on Acetylene Ignition | | | |
|---|---|---|---|---|
| $C_2H_2$ Pressure (ATM) | %$C_2H_3$ Br Added | %$C_2H_3$ Br Analyzed | Ignition Temp (K) | $\Delta T_i$ |
| 4.37 | 5.2 | .97 | 1422 | +122 |
| 7.86 | 5.0 | .49 | 1238 | +28 |
| 14.84 | 5.0 | .80 | 1169 | +22 |

It will be observed that the addition of vinyl bromide inhibits acetylene ignition at pressures of up to approximately 4.5 atm. At pressures of about 7 atm and above, vinyl bromide had no significant effect on the ignition behavior of acetylene. Gas chromatographic analysis of the mixture indicated that vinyl bromide may react with acetylene to a significant extent.

In the above example, the percent of $CO_2$ and inhibitors added to acetylene, i.e., nitric oxide, hydrogen halides and vinyl bromide, was determined from the partial pressure of the additive used to make the mixtures. In the cases of $CO_2$, NO and $C_2H_3Br$, the actual composition of the mixture was also determined by gas chromatographic analysis.

It will be readily seen from the foregoing that the present invention provides an improved method for stabilizing acetylene against explosive decomposition by mixing together with the acetylene a small amount of a chemical free-radical scavenging agent chosen from the group consisting of NO, HCl, HBr, HI and $C_2H_3Br$ as well as mixtures thereof. Moreover, the present invention provides a method for stabilizing acetylene by adding one or more of the chosen chemical inhibitors which lower the ignition temperatures of the acetylene mixtures so that the acetylene may now be more safely handled, shipped and stored in both sealed containers and pipelines. Furthermore, the present invention provides for a stabilized acetylene mixture containing a chemical inhibitor which makes it possible to safely handle, ship and store the acetylene and which at the same time increases the storage and shipping efficiency of the acetylene containers and pipelines by increasing the pressure of the acetylene which these containers and pipelines may now safely handle under ordinary conditions.

What is claimed is:

1. A method for stabilizing acetylene against explosive decomposition comprising mixing together with the acetylene a chemical free radical scavenging agent chosen from the group consisting of nitric oxide, hydrogen chloride, hydrogen bromide, hydrogen iodide and vinyl bromide as well as mixtures thereof.

2. A method as defined by claim 1 wherein the chemical free radical scavenging agent is present in an amount ranging from about 0.5 to 10 percent in the mixture.

3. A method as defined by claim 1 wherein nitric oxide is mixed with acetylene in amounts of from about 1 to 10% and at acetylene partial pressures in excess of about 2 atm.

4. A method as defined by claim 1 wherein hydrogen chloride is mixed with acetylene in amounts of from about 1 to 5% and at acetylene partial pressures in excess of about 2 atm.

5. A method as defined by claim 1 wherein hydrogen bromide is mixed with acetylene in amounts of from about 1 to 5% and at acetylene partial pressures in excess of about 2 atm.

6. A method as defined by claim 1 wherein hydrogen iodide is mixed with acetylene in an amount of about 5% and at acetylene partial pressures in excess of about 2 atm.

7. A method as defined by claim 1 wherein vinyl bromide is mixed with acetylene in an amount of about 5% and at acetylene partial pressures of up to about 4.5 atm.

* * * * *